(12) United States Patent
Tohyama et al.

(10) Patent No.: US 8,399,707 B2
(45) Date of Patent: Mar. 19, 2013

(54) 4-(TRICHLOROMETHYLTHIO) ANILINES, METHOD FOR PRODUCTION THEREOF, AND METHOD FOR PRODUCING 4-(TRIFLUOROMETHYLTHIO) ANILINES

(75) Inventors: Yoshitomo Tohyama, Hirakata (JP); Kengo Kanematsu, Chiba (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 492 days.

(21) Appl. No.: 12/667,543

(22) PCT Filed: Jul. 1, 2008

(86) PCT No.: PCT/JP2008/061901
§ 371 (c)(1),
(2), (4) Date: Jan. 4, 2010

(87) PCT Pub. No.: WO2009/008287
PCT Pub. Date: Jan. 15, 2009

(65) Prior Publication Data
US 2010/0331578 A1    Dec. 30, 2010

(30) Foreign Application Priority Data
Jul. 6, 2007    (JP) ................................ 2007-178577

(51) Int. Cl.
*C07C 211/44* (2006.01)
(52) U.S. Cl. ........................................................ 564/412
(58) Field of Classification Search ............ 564/412
See application file for complete search history.

(56) References Cited

U.S. PATENT DOCUMENTS

| | | | |
|---|---|---|---|
| 4,897,415 A | 1/1990 | Hubl et al. | |
| 5,449,681 A | 9/1995 | Wickiser | |
| 5,596,122 A | 1/1997 | Wickiser | |
| 5,614,525 A | 3/1997 | Wickiser | |
| 5,637,603 A | 6/1997 | Wickiser | |
| 2005/0159599 A1 | 7/2005 | Itoh et al. | |

FOREIGN PATENT DOCUMENTS

| | | |
|---|---|---|
| EP | 0 277 091 A2 | 8/1988 |
| EP | 0606756 A1 | 7/1994 |
| GB | 2042526 A | 9/1980 |
| GB | 2117375 A | 10/1983 |
| JP | 55-129263 A | 10/1980 |
| JP | 63-192772 A | 8/1988 |
| JP | 6-316518 | 11/1994 |
| JP | 11-049742 A | 2/1999 |
| JP | 2004-182716 A | 7/2004 |
| WO | WO 2006/099957 A1 | 9/2006 |
| WO | WO 2007/046513 | * 4/2007 |
| WO | WO 2007/046513 A2 | 4/2007 |
| WO | WO 2007/066496 A1 | 6/2007 |

OTHER PUBLICATIONS

Argyle, C. et al. "The Constitution and Reactions of Thiocarbonyl Tetrachloride. Part IV. Reaction with Secondary and Tertiary Amines", Journal of the Chemical Society, Chemical Society, Letchworth, Jan. 1, 1937, No. Part 4, pp. 1629-1634. XP002104247.
Communication (Supplementary EP Search Report) in EP Appln No. 08 79 0764 dated Oct. 26, 2011.
Kim, Y. et al. "Facile One-Pot Synthesis of x-Chloro Sulfoxides from Sulfides", Stuttgart, Feb. 1993, No. 2, pp. 209-210.
The International Search Report of the corresponding International Patent Application No. PCT/JP2008/061901, dated Aug. 26, 2008. (2 pgs.).
Laurent, "Selective aliphatic fluorination by halogen exchange in mild conditions", Journal of Fluorine Chemistry, vol. 127, No. 1, pp. 85-90, (2006).
Baruffini, et al., "4-Aminothiophenol derivatives of antifungal activity", Farmaco Edizione Scientifica, 1958. vol. 13, pp. 911-921.

* cited by examiner

Primary Examiner — Robert Havlin
(74) Attorney, Agent, or Firm — Foley & Lardner LLP

(57) ABSTRACT

There are provided a 4-(trichloromethylthio)aniline represented by the general formula (II):

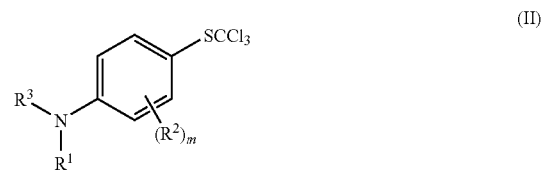

wherein $R^1$ represents a hydrogen atom or an alkyl group having 1 to 3 carbon atoms, $R^2$ each independently represents a halogen atom, an alkyl group having 1 to 3 carbon atoms, or a perfluoroalkyl group having 1 to 3 carbon atoms, $R^3$ represents a formyl group, an acetyl group, or a trifluoroacetyl group, and m represents an integer of 0 to 4, a method for producing the same, and a method for producing a 4-(trifluoromethylthio)aniline derivative using the 4-(trichloromethylthio)aniline. It becomes possible to produce a 4-(trifluoromethylthio)aniline with a high yield by using raw materials that can easily be obtained industrially and using general purpose production facilities.

6 Claims, No Drawings

4-(TRICHLOROMETHYLTHIO) ANILINES, METHOD FOR PRODUCTION THEREOF, AND METHOD FOR PRODUCING 4-(TRIFLUOROMETHYLTHIO) ANILINES

TECHNICAL FIELD

The present invention relates to 4-(trichloromethylthio)anilines useful as intermediates for the production of 4-(trifluoromethylthio)anilines, and to methods for the production thereof. And the present invention relates to methods for the production of 4-(trifluoromethylthio)anilines using the 4-(trichloromethylthio)anilines.

BACKGROUND ART 4-(Trifluoromethylthio)anilines are compounds useful as intermediates for the production of pesticides, such as insecticides and acaricides, as described, for example, in International Publication No. 06/099957 pamphlet (Patent Document 1), Japanese Patent Laying-Open No. 2004-182716 (Patent Document 2), and International Publication No. 07/046,513 pamphlet (Patent Document 3).

4-(Trifluoromethylthio)aniline can be produced by making 4-aminothiophenol and trifluoroiodomethane react under UV irradiation in presence of ammonia (European Patent Laying-Open No. 0277091 specification (Patent Document 4)).

However, the production method using a UV irradiation device is not necessarily a method useful in industrial production because the production facility is complex. Moreover, the boiling point of trifluoroiodomethane is so low ($-22.5°$ C.) that a complex production facility is required for the purpose of, for example, securing safety.

[Patent Document 1] International Publication No. 06/099957 pamphlet
[Patent Document 2] Japanese Patent Laying-Open No. 2004-182716
[Patent Document 3] International Publication No. 07/046,513 pamphlet
[Patent Document 4] European Patent Laying-Open No. 0277091 specification

DISCLOSURE OF THE INVENTION

Problems to be Solved by the Invention

The object of the present invention is to provide a method by which a 4-(trifluoromethylthio)aniline can be produced with a high yield by using industrially easily available raw materials and using general purpose production facilities.

Means for Solving the Problems

The present inventors found out that the aforementioned problem was solved by using 4-(trichloromethylthio)anilines as intermediates for the production of 4-(trifluoromethylthio)anilines. Moreover, they found a new method using a higher safe chlorinating agent, the method being suitable for industrial produce of 4-(trichloromethylthio)anilines with high yield. That is, the present invention is as follows.

The present invention provides a method for producing a 4-(trichloromethylthio)aniline, including a step of making a 4-(methylthio)aniline represented by the general formula (I):

[Chem. 1]

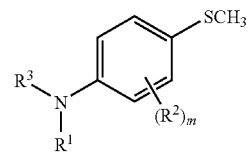

wherein $R^1$ represents a hydrogen atom or an alkyl group having 1 to 3 carbon atoms, $R^2$ each independently represents a halogen atom, an alkyl group having 1 to 3 carbon atoms, or a perfluoroalkyl group having 1 to 3 carbon atoms, $R^3$ represents a formyl group, an acetyl group, or a trifluoroacetyl group, and m represents an integer of 0 to 4, react with sulfuryl chloride to obtain a 4-(trichloromethylthio)aniline represented by the general formula (II):

[Chem. 2]

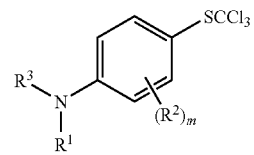

wherein $R^1$, $R^2$, $R^3$, and m are the same in meaning as those defined above.

The present invention also provides a method for producing a 4-(trifluoromethylthio)aniline, including steps of:

making a 4-(methylthio)aniline represented by the general formula (I):

[Chem. 3]

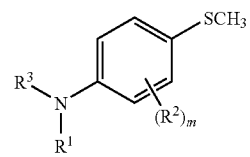

wherein $R^1$ represents a hydrogen atom or an alkyl group having 1 to 3 carbon atoms, $R^2$ each independently represents a halogen atom, an alkyl group having 1 to 3 carbon atoms, or a perfluoroalkyl group having 1 to 3 carbon atoms, $R^3$ represents a formyl group, an acetyl group, or a trifluoroacetyl group, and m represents an integer of 0 to 4, react with sulfuryl chloride to obtain a 4-(trichloromethylthio)aniline represented by the general formula (II):

[Chem. 4]

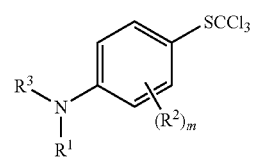

wherein $R^1$, $R^2$, $R^3$, and m are the same in meaning as those defined above, and making the 4-(trichloromethylthio)aniline represented by the general formula (II) react with a fluorinating agent to obtain a 4-(trifluoromethylthio)aniline represented by the general formula (III):

[Chem. 5]

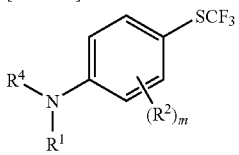

(III)

wherein $R^1$, $R^2$, and m are the same in meaning as those defined above, and $R^4$ represents a hydrogen atom, a formyl group, an acetyl group, or a trifluoroacetyl group. As the fluorinating agent, hydrogen fluoride and/or a hydrogen fluoride-amine complex can be preferably used.

The present invention also provides a 4-(trichloromethylthio)aniline represented by the general formula (II):

[Chem. 6]

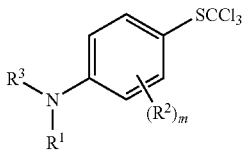

(II)

wherein $R^1$ represents a hydrogen atom or an alkyl group having 1 to 3 carbon atoms, $R^2$ each independently represents a halogen atom, an alkyl group having 1 to 3 carbon atoms, or a perfluoroalkyl group having 1 to 3 carbon atoms, $R^3$ represents a formyl group, an acetyl group, or a trifluoroacetyl group, and m represents an integer of 0 to 4.

In the present invention, $R^3$ in the general formulae (I) and (II) preferably an acetyl group.

Effects of the Invention

According to the present invention, since 4-(trichloromethylthio)anilines are used as intermediates for the production of 4-(trifluoromethylthio)anilines, 4-(trifluoromethylthio)anilines can be produced with high yield by using industrially easily available and higher safe reagents and using comparatively simple facilities. According to the present invention, 4-(trichloromethylthio)anilines can be produced with high yield by a method suitable for industrial production.

BEST MODES FOR CARRYING OUT THE INVENTION 4-(Trichloromethylthio)anilines

A 4-(trichloromethylthio)aniline of the present invention is represented by the following general formula (II).

[Chem. 7]

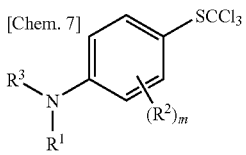

(II)

By using of the 4-(trichloromethylthio)aniline of the present invention as an intermediate, a 4-(trifluoromethylthio)aniline can be obtained with a high yield by using comparatively simple production facilities and a comparatively simple method.

In the general formula (II), $R^1$ is a hydrogen atom or an alkyl group having 1 to 3 carbon atoms. Specifically, the alkyl group having 1 to 3 carbon atoms is a methyl group, an ethyl group, a n-propyl group, and an isopropyl group. $R^2$ represents a halogen atom, an alkyl group having 1 to 3 carbon atoms, or a perfluoroalkyl group having 1 to 3 carbon atoms. Specific examples of the halogen atom include F, Cl, Br, and I atoms. Specific examples of the alkyl group having 1 to 3 carbon atoms include a methyl group, an ethyl group, a propyl group, and an isopropyl group. Specific examples of the perfluoroalkyl group having 1 to 3 carbon atoms include a trifluoromethyl group and a pentafluoroethyl group. m, representing the number of $R^2$, is an integer of 0 to 4. $R^2$ can be bonded to any position selected from among the 2-, 3-, 5- and 6-positions of the benzene ring. When the 4-(trichloromethylthio)aniline represented by the general formula (II) has two or more $R^2$s, those $R^2$s may be same or different.

$R^3$ represents a formyl group, an acetyl group, or a trifluoroacetyl group, and it plays a role as a protective group of an amino group or an alkyl-substituted amino group in the method for producing the 4-(trichloromethylthio)aniline of the present invention. While $R^3$ can be any group selected from among a formyl group, an acetyl group, and a trifluoroacetyl group, $R^3$ is preferably an acetyl group or a formyl group, and more preferably an acetyl group in consideration of the yield and the purity of the 4-(trichloromethylthio)aniline to be obtained. Considering the yield and the purity of the 4-(trifluoromethylthio)aniline when the 4-(trifluoromethylthio)aniline is prepared from the 4-(trichloromethylthio)aniline, $R^3$ is preferably an acetyl group or a trifluoroacetyl group, and more preferably an acetyl group. When an amino group or an alkyl-substituted amino group is protected by none of those groups or when an amino group or an alkyl-substituted amino group is protected by a protective group other than those mentioned above, little 4-(trichloromethylthio)aniline is produced, or even if 4-(trichloromethylthio)aniline is produced, its yield and purity are much lower.

Next, a method for producing the 4-(trichloromethylthio)aniline of the present invention is described. While the 4-(trichloromethylthio)aniline of the present invention can be prepared by any method, the following method can be used suitably for its production. Namely, the method is one that makes a 4-(methylthio)aniline represented by the general formula (I):

[Chem. 8]

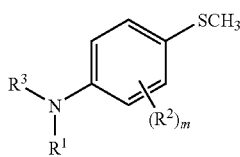

(I)

chlorinate by using sulfuryl chloride. $R^1$, $R^2$, $R^3$, and m in the general formula (I) are the same in meaning as those in the general formula (II). Hereafter, a method for producing the 4-(trichloromethylthio)aniline of the general formula (II) from the 4-(methylthio)aniline of the general formula (I) by using sulfuryl chloride is described in detail.

While the amount of sulfuryl chloride to be used in the chlorination reaction is theoretically 3 equivalents to the 4-(methylthio)aniline of the general formula (I), it may be either increased or decreased appropriately depending upon the condition of the reaction. Specifically, the amount of sulfuryl chloride to be used is usually 3 to 10 mol, and preferably 3 to 4 mol per mol of the 4-(methylthio)aniline of the general formula (I).

While the chlorination reaction may be performed without using a solvent, it is usually performed in the presence of a solvent. Examples of the solvent include aromatic hydrocarbons such as toluene and xylene, halogenated aromatic hydrocarbons such as chlorobenzene, aliphatic hydrocarbons such as hexane and heptane, halogenated aliphatic hydrocarbons such as chloroform, ethers such as dioxane and tetrahydrofuran, esters such as ethyl acetate, and ketones such as methyl isobutyl ketone. Considering the reactivity of the chlorination reaction and so on, aromatic hydrocarbons such as toluene and xylene, halogenated aromatic hydrocarbons such as chlorobenzene, and halogenated aliphatic hydrocarbons such as chloroform are preferable as the solvent, and toluene, xylene, chlorobenzene and so on are more preferable. While the amount of the solvent to be used is not particularly restricted, it may be, for example, about 0.5 to about 50 parts by mass per part by mass of the 4-(methylthio)aniline of the general formula (I), and it is preferably about 1 to about 20 parts by mass, and more preferably about 1 to about 10 parts by mass.

The reaction temperature of the chlorination reaction is usually from −20 to 100° C., and preferably within the range of from 0 to 80° C. While preferable reaction time varies depending upon the reaction temperature, the amount of sulfuryl chloride to be used, and so on, usually, it is from a moment to 100 hours and, typically, it is within the range of about 1 hour to about 24 hours.

The progress of the reaction can be checked by taking out a part of a reaction mixture and qualitatively or quantitatively analyzing the amounts of the 4-(methylthio)aniline of the general formula (I) and the 4-(trichloromethylthio)aniline of the general formula (II) present in the reaction mixture by using such an analytic technique as thin layer chromatography, gas chromatography, and high-performance liquid chromatography. While a monochlorinated substance and a dichlorinated substance of the 4-(methylthio)aniline are formed as intermediates during the chlorination reaction, the amounts of these intermediates during the reaction can also be analyzed by the above-mentioned analytic technique.

According to the chlorination method in accordance with the present invention, the 4-(trichloromethylthio)aniline of the general formula (II) can be obtained with a high yield and a high purity by an industrially advantageous procedure. The chlorination method of the present invention makes it possible to produce the 4-(trichloromethylthio)aniline of the general formula (II) with a high purity while causing less chlorination of the benzene ring and, when $R^2$ is an alkyl group, less chlorination of the alkyl group.

The reaction mixture after the completion of the reaction may be subjected to the following preparation of a 4-(trifluoromethylthio)aniline as it is or alternatively may be subjected to isolation of the 4-(trichloromethylthio)aniline of the general formula (II) through the post-treatment steps described below:

(a) a step of removing unreacted sulfuryl chloride from the reaction mixture, (b) a step of washing the reaction mixture with water, an aqueous alkaline solution, saturated brine, and so on, and (c) a step of isolating the 4-(trichloromethylthio)aniline In step (a), the method for removing unreacted sulfuryl chloride can be, for example, 1) a method that blows inert gas (e.g., nitrogen and argon) into the reaction mixture, and 2) a method that partially concentrates the reaction mixture after, diluting with an organic solvent as needed. While the organic solvent to be used for the dilution is not particularly limited, examples thereof include aromatic hydrocarbons such as toluene and xylene, halogenated aromatic hydrocarbons such as chlorobenzene, aliphatic hydrocarbons such as hexane and heptane, halogenated aliphatic hydrocarbons such as chloroform, ethers such as dioxane and tetrahydrofuran, esters such as ethyl acetate, ketones such as methyl isobutyl ketone, and mixtures thereof.

In step (b), the washing of the reaction mixture can be performed, for example, by using washing water such as water, an aqueous alkaline solution and saturated brine, after, diluting the reaction mixture with a hydrophobic organic solvent as needed. Examples of the hydrophobic organic solvent include esters such as ethyl acetate and butyl acetate, aliphatic hydrocarbons such as hexane and heptane, halogenated aliphatic hydrocarbons such as chloroform, aromatic hydrocarbons such as toluene and xylene, halogenated aromatic hydrocarbons such as chlorobenzene and dichlorobenzene, ketones such as methyl isobutyl ketone, and ethers such as tert-butyl methyl ether, diisopropyl ether, and methyl cyclopentyl ether, alcohols that separates from water, such as 4-methyl-2-pentanol and sec-butanol, and mixtures thereof. Examples of the aqueous alkaline solution include an aqueous sodium hydroxide solution and an aqueous sodium hydrogencarbonate solution.

Examples of the method for isolating the 4-(trichloromethylthio)aniline in step (c) include 1) a method that sufficiently evaporates the washed organic layer, 2) a method that collects the solid formed in the washed organic layer by filtration after partially concentrating the organic layer as needed or thereafter cooling it as needed, and 3) a method that collects formed solid by filtration, which the solid is formed by pouring the washed organic layer, that may be partially concentrated, to a proper ratio mixture of water and hydrophilic organic solvent, and being cooled as needed. While the hydrophilic organic solvent is not particularly restricted, alcohols such as methanol, ethanol, isopropanol, and tert-butyl alcohol, can be used.

The solid (the 4-(trichloromethylthio)aniline) collected by filtration can be used for the next step, the preparation of a 4-(trifluoromethylthio)aniline, after being dried or undried. The isolated, dried or undried solid may be further purified by, for example, recrystallization, column chromatography, or washing with water or a poor solvent and so on. Examples of the poor solvent include aliphatic hydrocarbons such as hexane and heptane, aromatic hydrocarbons such as toluene and xylene, halogenated aromatic hydrocarbons such as chlorobenzene and dichlorobenzene, ethers such as tert-butyl methyl ether, diisopropyl ether, and methyl cyclopentyl ether, and mixtures thereof.

One or two or more steps among steps (a) through (c) may be omitted. In one possible embodiment, step (b) is performed without blowing inert gas into the reaction mixture or partially concentrating the reaction mixture, thereby decomposing and removing unreacted sulfuryl chloride with contact of water or an aqueous alkaline solution during the washing. In another possible embodiment, a reaction mixture from which unreacted sulfuryl chloride has been removed is used for the next step, i.e. the preparation of a 4-(trifluoromethylthio)aniline without performing steps (b) and (c) or step (c).

Next, the method for producing the 4-(methylthio)aniline represented by the general formula (I) is described. The 4-(methylthio)aniline represented by the general formula (I) can be prepared through, for example, the below mentioned Reactions (A-1) and (A-2), Reactions (B-1) and (B-2).

[Chem. 9]

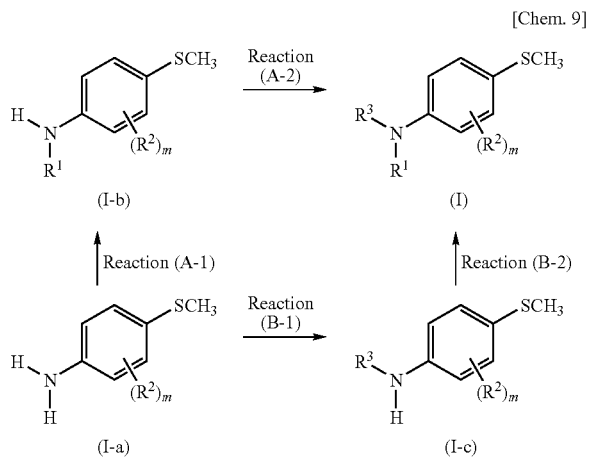

$R^1$, $R^2$, $R^3$, and m in compounds (I-a), (I-b) and (I-c) are the same in meaning as those in the general formula (I).

Reaction (A-1) is not performed when $R^1$ in the general formula (I) is a hydrogen atom. The alkylation of Reaction (A-1) when $R^1$ is an alkyl group having 1 to 3 carbon atoms can be performed by making Compound (I-a) and a compound represented by the following general formula (IV):

$$R^5—Y \quad (IV)$$

(hereinafter, referred to as Compound (IV)) react with each other. $R^5$ in the general formula (IV) is an alkyl group having 1 to 3 carbon atoms, and Y represents a leaving group.

Examples of the leaving group Y include a chlorine atom, a bromine atom, an iodine atom, $CH_3SO_3—$, p-$CH_3C_6H_4SO_3—$ and $CH_3OSO_3—$. Specific examples of Compound (IV) include dimethyl sulfate, methyl iodide, ethyl methanesulfonate, ethyl bromide, isopropyl chloride, and propyl p-toluenesulfonate.

The alkylation of Reaction (A-1) is usually performed in the presence of a base, in a solvent. Examples of the solvent include ketones such as acetone, methyl ethyl ketone and methyl isobutyl ketone, aromatic hydrocarbons such as benzene, toluene and xylene, aliphatic hydrocarbons such as hexane and heptane, ethers such as diethyl ether, tert-butyl methyl ether, tetrahydrofuran, 1,4-dioxane, 1,2-dimethoxyethane, 1,2-diethoxyethane and cyclopentyl methyl ether, halogenated hydrocarbons such as chloroform, chlorobenzene and dichlorobenzene, nitriles such as acetonitrile and propionitrile, aprotic polar solvents such as N,N-dimethylformamide, N,N-dimethylacetamide, 1-methyl-2-pyrrolidone, 1,3-dimethylimidazolinone, and dimethyl sulfoxide, water, and mixtures thereof.

Examples of the base include hydroxides of alkali metals or alkaline earth metals, such as sodium hydroxide, potassium hydroxide and calcium hydroxide, hydrides of alkali metals or alkaline earth metals such as sodium hydride, potassium hydride and calcium hydride, carbonates of alkali metals or alkaline earth metals such as sodium carbonate and potassium carbonate, alcoholates of alkali metals such as sodium ethylate and sodium methylate, organolithium reagents such as n-butyl lithium and lithium diisopropylamide, and organic bases such as triethylamine, pyridine, and 1,8-diazabicyclo[5.4.0]-7-undecene.

While the amount of Compound (IV) to be used is not particularly limited and Compound (IV) may be used as a reaction solvent when Compound (IV) is liquid under the reaction condition, the amount of that compound is usually about 1 to about 10 mol, preferably about 2 to about 5 mol per mol of Compound (I-a). Moreover, the amount of the base to be used is also not particularly limited, and it is about 1 to about 10 mol, preferably about 2 to about 5 mol per mol of Compound (I-a).

The reaction temperature of the alkylation is usually within the range of from −78 to 150° C., preferably within the range of from 0 to 100° C. While the reaction time varies depending on the reaction temperature, it is usually within the range of from a moment to 100 hours.

After the completion of the reaction, Compound (I-b) can be isolated by performing ordinary post-treatment including, for example, pouring the reaction mixture into water, neutralizing as needed, then extracting with an organic solvent, and subsequently drying and concentrating the organic layer. The isolated Compound (I-b) may be further purified by recrystallization, column chromatography, and so on. Moreover, the isolated Compound (I-b) can also be used for the next step without being purified. Alternatively, the next step may be performed without performing a part or the whole of the post-treatment for the reaction mixture after the completion of the reaction.

The 4-(methylthio)aniline represented by the general formula (I) can be obtained by making Compound (I-b) react with a compound represented by the following general formula (V):

$$R^6_2O \quad (V)$$

(hereinafter, referred to as Compound (V)) when $R^3$ in the general formula (I) is an acetyl group or a trifluoroacetyl group; and can be obtained by using the method disclosed in Tetrahedron Letters, 23 (33), 3315 (1982) when $R^3$ in the general formula (I) is a formyl group (Reaction (A-2)). $R^6$ in the general formula (V) represents an acetyl group or a trifluoroacetyl group.

Reaction (A-2) may be performed in the presence or absence of a base, in the presence or absence of a solvent. Examples of the solvent include ketones such as acetone, methyl ethyl ketone and methyl isobutyl ketone, aromatic hydrocarbons such as benzene, toluene and xylene, aliphatic hydrocarbons such as hexane and heptane, ethers such as diethyl ether, tert-butyl methyl ether, tetrahydrofuran, 1,4-dioxane, 1,2-dimethoxyethane, 1,2-diethoxyethane and cyclopentyl methyl ether, halogenated hydrocarbons such as chloroform, chlorobenzene and dichlorobenzene, nitriles such as acetonitrile and propionitrile, aprotic polar solvents such as N,N-dimethylformamide, N,N-dimethylacetamide, 1-methyl-2-pyrrolidone, 1,3-dimethylimidazolinone, and dimethyl sulfoxide, water, and mixtures thereof.

Examples of the base include hydroxides of alkali metals or alkaline earth metals such as sodium hydroxide, potassium hydroxide and calcium hydroxide, hydrides of alkali metals or alkaline earth metals such as sodium hydride, potassium hydride and calcium hydride, carbonates of alkali metals or alkaline earth metals such as sodium carbonate and potassium carbonate, alcoholates of alkali metals such as sodium ethylate and sodium methylate, organolithium reagents such as n-butyl lithium and lithium diisopropylamide, and organic bases such as triethylamine, pyridine, and 1,8-diazabicyclo [5.4.0]-7-undecene.

While the using amounts of Compound (V) and the base are not particularly limited, they respectively are usually about 1 to about 6 mol per mol of Compound (I-b). The reaction temperature is usually within the range of from −78 to 150° C., preferably within the range of from 0 to 100° C. While the reaction time varies depending on the reaction temperature, it is usually within the range of from a moment to 100 hours.

After the completion of the reaction, the 4-(methylthio) aniline represented by the general formula (I) can be isolated by performing ordinary post-treatment including, for example, pouring the reaction mixture into water, neutralizing as needed, then extracting with an organic solvent, and subsequently drying and concentrating the organic layer. After the isolation, it may be further purified by recrystallization, column chromatography, and so on. Moreover, the isolated 4-(methylthio)aniline represented by the general formula (I) can also be used for the next step without being purified. Alternatively, the next step may be performed without a part or the whole of the post-treatment for the reaction mixture after the completion of the reaction.

The production of the 4-(trichloromethylthio)aniline of the general formula (I) by means of Reactions (B-1) and (B-2) differs from the production by means of Reactions (A-1) and (A-2) only in the order of introductions of $R^1$ and $R^3$, and the compound of the general formula (I) can be produced from Compound (I-a) basically in the same manner. It is noted that Reaction (B-2) is not performed when $R^1$ in the general formula (I) is a hydrogen atom.

Compound (I-a) is a compound disclosed in Japanese Patent Laying-Open No. 55-129263 and can be produced easily from industrially available compounds. For example as shown below, it can be produced by 1) a reaction of a mercaptoaniline (Compound (I-d)) with dimethyl sulfate or methyl iodide (Reaction (C-1)) and 2) a method that includes obtaining a thiocyanoaniline (Compound I-f) by a reaction of an aniline (Compound (I-e)) with a thiocyanate and subsequently converting the thiocyano group into a methylthio group under an alkali condition (Reaction (D-1)).

[Chem. 10]

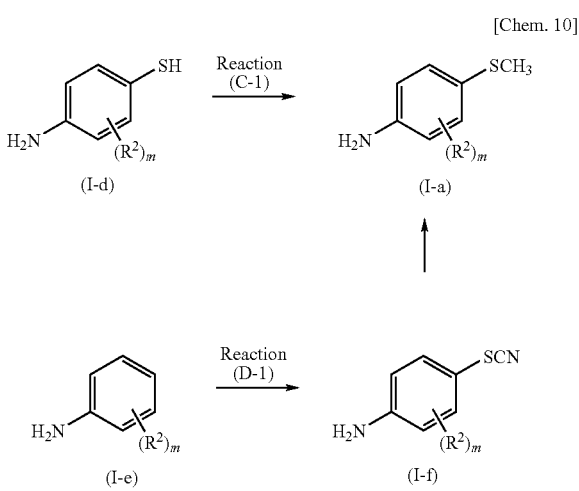

4-(Trifluoromethylthio)aniline

A 4-(trifluoromethylthio)aniline related to the present invention is a compound represented by the following general formula (III).

[Chem. 11]

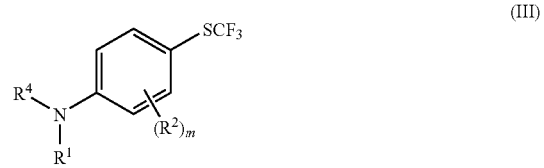

The 4-(trifluoromethylthio)aniline can be produced efficiently from the aforementioned 4-(trichloromethylthio) aniline of the general formula (II) of the present invention.

$R^1$, $R^2$, and m in the general formula (III) are the same in meaning as those in the general formula (II). $R^4$ represents a hydrogen atom, a formyl group an acetyl group, or a trifluoroacetyl group. The 4-(trifluoromethylthio)aniline represented by the general formula (III) may be a mixture of a compound in which $R^4$ is a hydrogen atom and a compound in which $R^4$ is a formyl group, an acetyl group, or a trifluoroacetyl group.

The 4-(trifluoromethylthio)aniline represented by the general formula (III) can be produced from the aforementioned 4-(trichloromethylthio)aniline represented by the general formula (II) of the present invention by using a conventionally known fluorinating agent. As the 4-(trichloromethylthio) aniline represented by the general formula (II), one produced by the aforementioned production method of the present invention can suitably be used.

While the fluorinating agent is not particularly restricted, HF (hydrogen fluoride), HF-amine complexes, and mixtures thereof can be used, for example. Examples of the HF-amine complexes include pyridine-HF and triethylamine-HF. The ratio of amine to HF is not particularly restricted. While the amount of the fluorinating agent to be used is theoretically 3 equivalents to the 4-(trichloromethylthio)aniline of the general formula (II), it may be either increased or decreased appropriately depending upon the condition of the reaction. Specifically, when the fluorinating agent is HF, the amount of HF to be used is usually 3 to 100 mol per mol of the 4-(trichloromethylthio)aniline of the general formula (II). The surplus HF and/or HF-amine complex can also be collected and reused.

The fluorination reaction may be performed in the presence of a catalyst and a solvent. Examples of the catalyst include metal halides such as antimony fluoride. The amount of the catalyst to be used can be from a catalytic amount to an excessive amount (for example, about 0.001 to about 10 mol, preferably about 0.01 to about 1 mol) per mol of the 4-(trichloromethylthio)aniline of the general formula (II).

Examples of the solvent include aromatic hydrocarbons such as toluene and xylene, halogenated aromatic hydrocarbons such as chlorobenzene, aliphatic hydrocarbons such as hexane and heptane, halogenated aliphatic hydrocarbons such as chloroform, ethers such as dioxane and tetrahydrofuran, esters such as ethyl acetate, and ketones such as methyl isobutyl ketone. Considering the reactivity of the fluorination reaction and so on, the solvent is preferably, an aromatic hydrocarbon such as toluene and xylene, a halogenated aromatic hydrocarbon such as chlorobenzene, and a halogenated aliphatic hydrocarbon such as chloroform, and more preferably toluene, xylene, chlorobenzene, and so on. While the amount of the solvent to be used is not particularly restricted, it may be, for example, from about 0.5 to about 30 parts by mass per part by mass of the 4-(trichloromethylthio)aniline of the general formula (II). Preferably, it is from about 1 to about 10 parts by mass.

The reaction temperature of the fluorination reaction is usually −20 to 100° C. when the fluorinating agent is HF, and it is usually within the range of from 100 to 250° C. when the fluorinating agent is an HF-amine complex such as a pyridine-HF complex. While a preferable reaction time varies depending upon the reaction temperature, the amounts of the fluorinating agent and the catalyst to be used, and so on, it is usually from a moment to 100 hours and is typically within the range of about 1 hour to about 24 hours. The fluorination reaction may be performed under pressure by the use of a pressure reactor such as an autoclave.

The progress of the reaction can be checked by taking out a part of a reaction mixture and qualitatively or quantitatively analyzing the amounts of the 4-(trichloromethylthio)aniline of the general formula (II) and the 4-(trifluoromethylthio) aniline of the general formula (III) present in the reaction mixture by using such an analytic technique as thin layer chromatography and high-performance liquid chromatography. While a monofluorinated substance and a difluorinated substance of the 4-(trichloromethylthio)aniline are formed as intermediates during the fluorination reaction, the amounts of these intermediates during the reaction can also be analyzed by the above-mentioned analytic technique. In the fluorination reaction, a monofluorinated substance and/or a difluorinated substance of the 4-(trichloromethylthio)aniline may also be obtained through the adjustment of the reaction temperature of the fluorination reaction, the amount of the fluorinating agent, and so on. In the fluorination reaction, while the protective group (a formyl group, an acetyl group, or a trifluoroacetyl group) of an amino group or an alkyl-substituted amino group is deprotected under some reaction conditions or some conditions in post-treatment, the 4-(trifluoromethylthio)aniline of the general formula (III) in this case is obtained as a mixture of a compound having the protective group and a compound having no protective group, or singly as a compound having no protective group above.

The reaction mixture after the completion of the reaction may be subjected to a production process of a pesticide and so on, or alternatively may be subjected to isolation of the 4-(trifluoromethylthio)aniline of the general formula (III) through the post-treatment steps described below:

(i) a step of washing the reaction mixture with water, an aqueous alkaline solution, saturated brine, and so on, and (ii) a step of isolating the 4-(trifluoromethylthio)aniline.

In step (i), the washing of the reaction mixture can be performed, for example, by using washing water, such as water, an aqueous alkaline solution and saturated brine, after diluting the reaction mixture with a hydrophobic organic solvent as needed. As the hydrophobic organic solvent, those disclosed previously to use for the 4-(trichloromethylthio) aniline of the general formula (II) may be used.

Examples of the method for isolating the 4-(trifluoromethylthio)aniline in the above-mentioned step (ii) include 1) a method that sufficiently evaporates the washed organic layer, 2) a method that collects the solid formed in the washed organic layer by filtration after partially concentrating the organic layer as needed or thereafter cooling it as needed, 3) a method that collects formed solid by filtration, which the solid is formed by pouring the washed organic layer, that may be partially concentrated, to a proper ratio mixture of water and hydrophilic organic solvent, and being cooled as needed, and 4) a method that concentrates the washed organic layer and distilling the concentrate. As to the hydrophilic organic solvent, those disclosed to use for the 4-(trichloromethylthio) aniline of the general formula (II) may be used.

The solid (the 4-(trifluoromethylthio)aniline) collected by filtration either can be used for production processes of a pesticide after being dried or undried. The isolated, dried or undried solid may be further purified by, for example, recrystallization, column chromatography, or washing with water or a poor solvent and so on. Examples of the poor solvent include aliphatic hydrocarbons such as hexane and heptane, aromatic hydrocarbons such as toluene and xylene, halogenated aromatic hydrocarbons such as chlorobenzene and dichlorobenzene, ethers such as tert-butyl methyl ether, diisopropyl ether and methyl cyclopentyl ether, and mixtures thereof.

The present invention is described in more detail below with Examples and Comparative Examples, but the present invention is not limited thereto.

Production Example 1

Synthesis of 2-fluoro-4-methylthioaniline-1

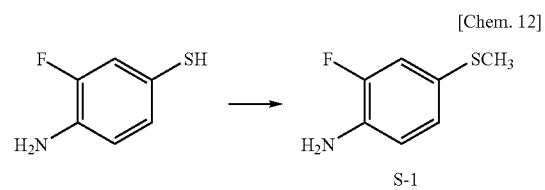

[Chem. 12]

To a mixture of 59.79 g of 2-fluoro-4-mercaptoaniline, 167.01 g of tert-butyl methyl ether, and 59.79 g of methyl iodide was dropped 43.72 g of triethylamine over 45 minutes while internal temperature was controlled at 20 to 30° C. After stirring it at room temperature for 2 hours, 150.16 g of water was poured and then the resulting mixture was made phase-separation. The aqueous layer was extracted with 105 g of tert-butyl methyl ether twice, and the combined organic layer was dried over magnesium sulfate and then concentrated. The residue was purified by silica gel column chromatography, so that 57.88 g of 2-fluoro-4-methylthioaniline (Compound S-1) was obtained.

The $^1$H-NMR data of Compound S-1 obtained are as follows:

$^1$H-NMR (CDCl$_3$, TMS) δ (ppm): 2.43 (s, 3H), 3.6-3.8 (br, 2H), 6.66-6.73 (m, 1H), 6.93-7.02 (m, 2H).

Production Example 2

Synthesis of N-acetyl-2-fluoro-4-methylthioaniline

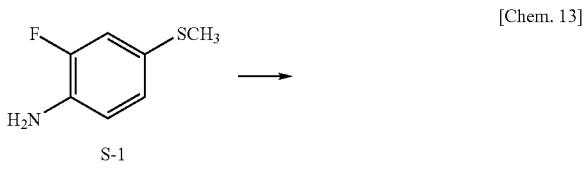

[Chem. 13]

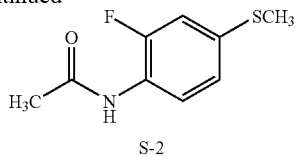

S-2

To 40.41 g of Compound S-1 was dropped 26.24 g of acetic anhydride over 1.5 hours under stirring with ice-cooling. After stirring it at room temperature for one hour, 40 g of tert-butyl methyl ether was added and the resulting mixture was stirred further at internal temperature of 20 to 25° C. for 2 hours. To the reaction mixture were added 400 g of ethyl acetate and 80 g of water, and then the resulting mixture was made phase-separation at an internal temperature of 45 to 51° C. The organic layer was washed twice with 80 g of saturated aqueous sodium bicarbonate solution. The organic layer was dried over magnesium sulfate and then concentrated. The residue (49.02 g) was washed twice with 50 g of hexane and dried, so that 48.60 g of N-acetyl-2-fluoro-4-methylthioaniline (Compound S-2) was obtained.

The $^1$H-NMR data of Compound S-2 obtained are as follows.

$^1$H-NMR (CDCl$_3$, TMS) δ (ppm): 2.21 (s, 3H), 2.46 (s, 3H), 6.98-7.03 (m, 2H), 7.34 (br, 1H), 8.16-8.21 (m, 1H).

Production Example 3

Synthesis of N-acetyl-N-methyl-2-fluoro-4-methylthioaniline

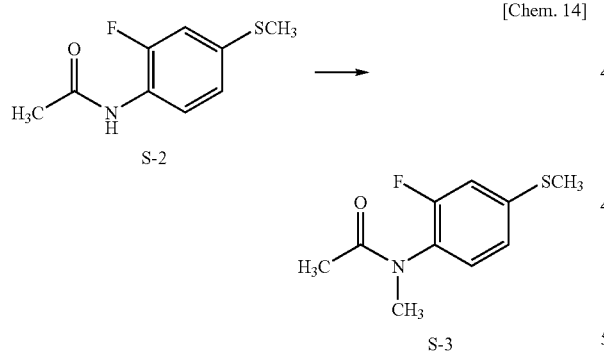

[Chem. 14]

To a mixture of 3.05 g of Compound S-2, 8.97 g of acetone, and 2.09 g of potassium carbonate was dropped 2.38 g of dimethyl sulfate at room temperature, and then the resulting mixture was heated to 54° C. and stirred it for 50 hours. During the stirring, 2.97 g of dimethyl sulfate, 2.08 g of potassium carbonate and 4.46 g of acetone were added. The mixture was cooled to room temperature, and 38 g of water and 20 g of ethyl acetate were added thereto, followed by making phase-separation. The aqueous layer was extracted with 20 g of ethyl acetate, which was then combined with oil layer and dried over magnesium sulfate. The oil layer was concentrated under reduced pressure, so that 3.32 g of a product containing N-acetyl-N-methyl-2-fluoro-4-methylthioaniline (Compound S-3) was obtained. The product was analyzed by gas chromatography (hereinafter, GC) to be found that the GC area percentage of Compound S-3 was 97.9%.

The $^1$H-NMR data of Compound S-3 obtained are as follows.

$^1$H-NMR (CDCl$_3$, TMS) δ (ppm): 1.87 (s, 3H), 2.51 (s, 3H), 3.20 (s, 3H), 7.0-7.1 (m, 2H), 7.1-7.2 (m, 1H).

Production Example 4

Synthesis of 2-fluoro-4-thiocyanoaniline

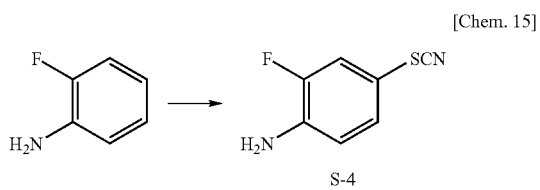

[Chem. 15]

To a mixed liquid of 210.9 g of sodium thiocyanate and 200.9 g of methanol was dropped a solution composed of 60.2 g of sodium bromide, 166.6 g of methanol and 163.7 g of bromine over 90 minutes while internal temperature was controlled at −10 to −6° C. To the mixed liquid was dropped 100.0 g of 2-fluoroaniline over 50 minutes while internal temperature was controlled at −10 to −5° C. The resulting mixture was stirred at the same temperature for 3 hours and then was poured into 784 g of water cooled to 0° C. The resulting mixture was neutralized with sodium carbonate and then was extracted twice with 196 g of chloroform. The organic layer was dried over magnesium sulfate and then concentrated, so that 151.9 g of 2-fluoro-4-thiocyanoaniline (Compound S-4) was obtained.

Production Example 5

Synthesis of 2-fluoro-4-methylthioaniline-2

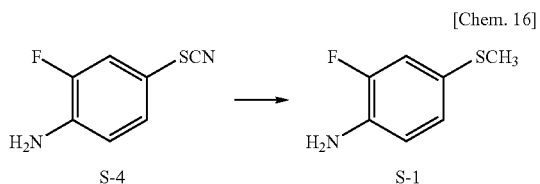

[Chem. 16]

To a mixture of 1.93 g of Compound S-4 and 5.68 g of methanol was dropped a mixture of 0.45 g of sodium hydroxide and 5.68 g of methanol at room temperature over 65 minutes, and then the resulting mixture was heated to 55 to 60° C. and stirred for 2 hours. The resulting reactant was analyzed by high performance liquid chromatography (hereinafter, HPLC) to be found that the HPLC area percentage of 2-fluoro-4-methylthioaniline (Compound S-1) was 75.9%.

Example 1

Synthesis of N-acetyl-2-fluoro-4-trichloromethylthioaniline-1

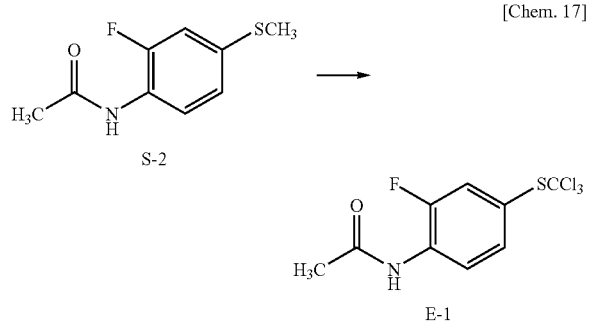

[Chem. 17]

To a mixture of 3.03 g of Compound S-2 and 9.0 g of chloroform was dropped a mixture of 6.34 g of sulfuryl chloride and 9.0 g of chloroform at room temperature over 10 minutes. Subsequently, the resulting mixture was heated to 60° C. and stirred for 4 hours. During the stirring, 3.05 g of chloroform and 0.46 g of sulfuryl chloride were added. After cooling it to room temperature, the reaction mixture was poured into 17.9 g of water. Subsequently, 36.8 g of ethyl acetate and 10.1 g of water were added thereto, followed by making phase-separation. The aqueous layer was further extracted twice with 9 g of ethyl acetate. The organic layers were combined, and then washed successively with 20.8 g of saturated aqueous sodium bicarbonate solution and 20 g of saturated brine. The organic layer was dried over magnesium sulfate and then concentrated, so that a product (4.54 g) containing N-acetyl-2-fluoro-4-trichloromethylthioaniline (Compound E-1) was obtained. The product was analyzed by GC to be found that the GC area percentage of Compound E-1 was 97%. The product was further subjected to silica gel column chromatography, so that a purified product was obtained.

The $^1$H-NMR data of Compound E-1 obtained are as follows:

$^1$H-NMR (CDCl$_3$, TMS) δ (ppm): 2.27 (s, 3H), 7.55 (dd, 1H, J=10.4, 2.0 Hz), 7.57 (d, 1H, J=7.6 Hz), 8.55 (dd, 1H, J=10.4, 7.6 Hz).

Example 2

Synthesis of N-acetyl-2-fluoro-4-trichloromethylthioaniline-2

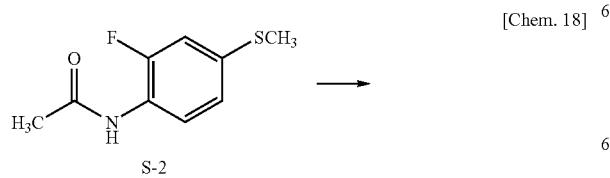

[Chem. 18]

-continued

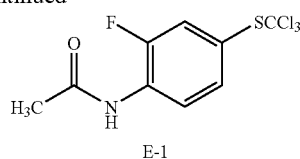

To a mixture of 3.02 g of Compound S-2 and 9.0 g of chlorobenzene was dropped a mixture of 6.75 g of sulfuryl chloride and 9.0 g of chlorobenzene at room temperature over 15 minutes. Subsequently, the resulting mixture was heated to 60 to 65° C. and stirred for 3 hours. During the stirring, 0.07 g of sulfuryl chloride was added. Subsequently, after cooling it to room temperature, 42.1 g of ethyl acetate and 12 g of water were added thereto, following by making phase-separation. The aqueous layer was further extracted twice with 9 g of ethyl acetate. The organic layers were combined, and then washed successively with 9.0 g of saturated aqueous sodium bicarbonate solution and 9.0 g of saturated brine. The organic layer was dried over magnesium sulfate and then concentrated, so that a product (4.49 g) containing N-acetyl-2-fluoro-4-trichloromethylthioaniline (Compound E-1) was obtained. The product was analyzed by GC to be found that the GC area percentage of Compound E-1 was 99%.

Referential Example 1

Synthesis of N-acetyl-2-fluoro-4-trichloromethylthioaniline-3

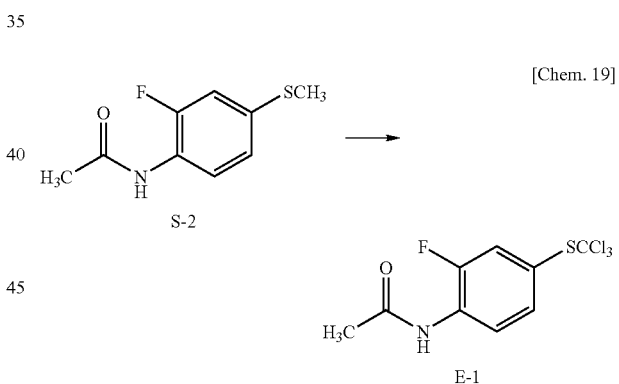

[Chem. 19]

A mixture of 30.2 g of Compound S-2 and 299 g of monochlorobenzene was irradiated with light (light source: 250 W high-pressure mercury lamp) at room temperature. Then, 45.4 g of chlorine gas was blown into the mixture in 7.5 hours with stirring. After blowing nitrogen gas into the reaction mixture to replace the gas in the system with nitrogen, 180 g of ethyl acetate and 120 g of water were added, and then a 5% aqueous sodium hydroxide solution was added until the pH of the aqueous layer became 6. After phase-separation, the organic layer was dried over magnesium sulfate and then concentrated. The residue was washed three times with 40 g of diisopropyl ether, so that 31.8 g of a product containing N-acetyl-2-fluoro-4-trichloromethylthioaniline (Compound E-1) was obtained. The product was analyzed by GC to be found that the GC area percentage of Compound E-1 was 90%.

Example 3

Synthesis of N-acetyl-N-methyl-2-fluoro-4-trichloromethylthioaniline

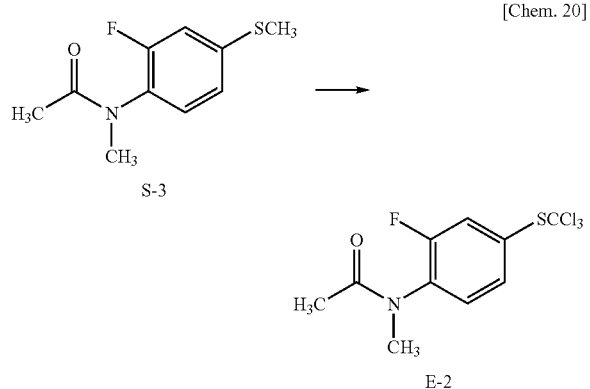

[Chem. 20]

To a mixture of 1.08 g of N-acetyl-N-methyl-2-fluoro-4-methylthioaniline (Compound S-3) and 3.20 g of chlorobenzene was dropped a mixture of 2.25 g of sulfuryl chloride and 3.20 g of chlorobenzene at room temperature over 35 minutes. The mixture was heated to 60 to 65° C. and then stirred for 4 hours. Zero point one one (0.11) g of sulfuryl chloride was added, and the mixture was stirred at the same temperature for 2 hours. After the mixture was cooled to room temperature, 6.3 g of water was added to wash the mixture, followed by making phase-separation. The aqueous layer was further extracted twice with 3.2 g of chlorobenzene. The organic layers were combined, and then washed successively with 6.3 g of saturated aqueous sodium bicarbonate solution and 12.4 g of saturated brine. The organic layer was dried over magnesium sulfate and then concentrated, so that 1.52 g of a product containing N-acetyl-N-methyl-2-fluoro-4-trichloromethylthioaniline (Compound E-2) was obtained. The product was analyzed by GC to be found that the GC area percentage of Compound E-2 was 92%. The product was further subjected to silica gel column chromatography, so that a purified product was obtained.

The $^1$H-NMR data of Compound E-2 obtained are as follows:

$^1$H-NMR (CDCl$_3$, TMS) δ (ppm): 1.92 (bs, 3H), 3.28 (bs, 3H), 7.3-7.5 (m, 1H), 7.6-7.7 (m, 2H).

Referential Example 2

Synthesis of N-acetyl-N-methyl-2-fluoro-4-trichloromethylthioaniline-2

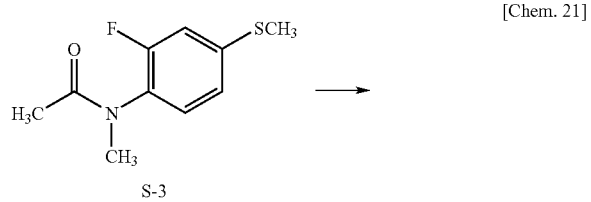

[Chem. 21]

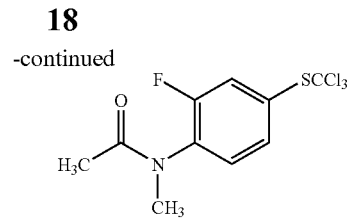

A mixture of 2.15 g of N-acetyl-N-methyl-2-fluoro-4-methylthioaniline (Compound S-3) and 21.3 g of chloroform was irradiated with light (light source: 250 W high-pressure mercury lamp) at room temperature. Then, 3.6 g of chlorine gas was blown into the mixture in 2.5 hours with stirring. After blowing nitrogen gas into the reaction mixture to replace the gas in the system with nitrogen, 12.8 g of ethyl acetate and 8.5 g of water were added, and then a 5% aqueous sodium hydroxide solution was added until the pH of the aqueous layer became 6. After phase-separation, the organic layer was dried over magnesium sulfate and then concentrated, so that 3.46 g of a product containing N-acetyl-N-methyl-2-fluoro-4-trichloromethylthioaniline (Compound E-2) was obtained. The product was analyzed by GC to be found that the GC area percentage of Compound E-2 was 49% and the GC area percentage of Compound S-3, which was a raw material, was 3.6%.

Example 4

Synthesis of N-trifluoroacetyl-2-fluoro-4-trichloromethylthioaniline

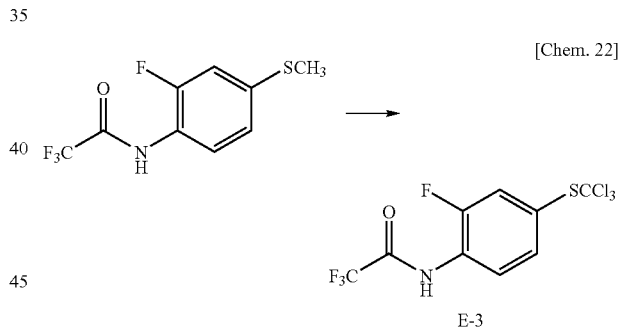

[Chem. 22]

To a mixture of 3.07 g of N-trifluoroacetyl-2-fluoro-4-methylthioaniline and 9.10 g of chlorobenzene was dropped a mixture of 5.40 g of sulfuryl chloride and 9.10 g of chlorobenzene at room temperature over 35 minutes. After the mixture was stirred at 20 to 25° C. for 20 hours, it was heated to 45° C. and was stirred for 3 hours. Zero point eight two (0.82) g of sulfuryl chloride was added, and the resulting mixture was stirred at that temperature for 2 hours, and then it was heated to 55° C. and stirred for 2 hours. Further, 0.82 g of sulfuryl chloride was added and the resulting mixture was stirred at that temperature for 17 hours. Then 1.63 g of sulfuryl chloride was added and the resulting mixture was stirred at that temperature for 2 hours. Further, 1.63 g of sulfuryl chloride was added and the resulting mixture was heated to 65° C. and stirred for 2 hours. After the mixture was cooled to room temperature, 18.2 g of water was added to wash the mixture, followed by making phase-separation. The aqueous layer was further extracted twice with 9.4 g of chlorobenzene. The organic layers were combined, and then washed with 13.80 g of a saturated aqueous sodium bicarbonate solution. The organic layer was dried over magnesium sulfate and then concentrated, so that 3.86 g of a product containing N-trifluoroacetyl-2-fluoro-4-trichloromethylthioaniline (Compound E-3) was obtained. The product was analyzed by GC to be found that the GC area percentage of Compound E-3 was 77%. The product was further subjected to silica gel column chromatography, so that a purified product was obtained.

The $^1$H-NMR data of Compound E-3 obtained are as follows:

$^1$H-NMR (CDCl$_3$, TMS) δ (ppm): 7.64-7.68 (m, 2H), 8.21 (bs, 1H), 8.49 (dd, 1H, J=8.0, 8.0 Hz).

Example 5

Synthesis of
N-formyl-2-fluoro-4-trichloromethylthioaniline

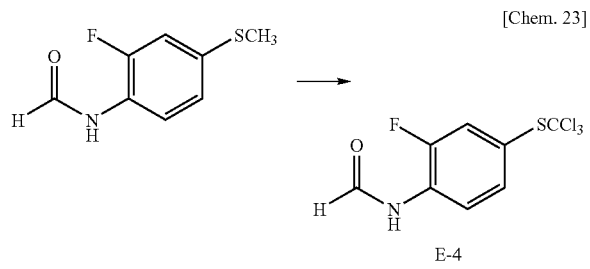

[Chem. 23]

To a mixture of 1.15 g of N-formyl-2-fluoro-4-methylthioaniline and 3.33 g of chlorobenzene was dropped a mixture of 2.67 g of sulfuryl chloride and 3.33 g of chlorobenzene at room temperature over 18 minutes. After the mixture was stirred at 20 to 25° C. for 1.5 hours, it was heated to 60 to 65° C. and was stirred for 3 hours. After the mixture was cooled to room temperature, the reaction mixture was added into 6.7 g of water and then 26.4 g of ethyl acetate was added and washed, followed by making phase-separation. The aqueous layer was further extracted twice with 5.0 g of ethyl acetate. The organic layers were combined, and washed successively with 5.0 g of saturated aqueous sodium bicarbonate solution and 5.0 g of saturated brine. The organic layer was dried over magnesium sulfate and then concentrated, so that 1.66 g of a product containing N-formyl-2-fluoro-4-trichloromethylthioaniline (Compound E-4) was obtained. The product was analyzed by GC to be found that the GC area percentage of Compound E-4 was 97%. The product was further subjected to silica gel column chromatography, so that 1.54 g of a purified product (GC area percentage 100%) was obtained.

The $^1$H-NMR data of Compound E-4 obtained are as follows:

$^1$H-NMR (CDCl$_3$, TMS) δ (ppm): 7.56-7.65 (m, 2H), 7.92 (bs, 1H), 8.53 (s, 1H), 8.56 (d, 1H, J=8.4 Hz).

Example 6

Synthesis of
N-acetyl-2-chloro-4-trichloromethylthioaniline

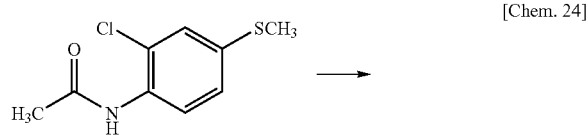

[Chem. 24]

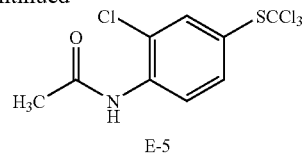

E-5

To a mixture of 4.31 g of N-acetyl-2-chloro-4-methylthioaniline and 12.94 g of chlorobenzene was dropped a mixture of 8.91 g of sulfuryl chloride and 12.94 g of chlorobenzene at room temperature over 80 minutes. After the mixture was stirred at 20 to 30° C. for 2 hours, it was heated to 40° C. and was stirred for 3 hours. After heating to 50° C. and stirring for 2 hours, 0.03 g of sulfuryl chloride was added and the resulting mixture was stirred at the same temperature for 1.5 hours. Further, 0.03 g of sulfuryl chloride was added and the resulting mixture was stirred at the same temperature for 1 hour. After the mixture was cooled to room temperature, the reaction mixture was added to 25.9 g of water and then 22.4 g of ethyl acetate was added and washed, followed by making phase-separation. The aqueous layer was further extracted twice with 12.9 g of ethyl acetate. The organic layers were combined, and then washed successively with 29.5 g of saturated aqueous sodium bicarbonate solution and 22.9 g of saturated brine. The organic layer was dried over magnesium sulfate and then concentrated, so that 6.20 g of a product containing N-acetyl-2-chloro-4-trichloromethylthioaniline (Compound E-5) was obtained. The product was analyzed by GC to be found that the GC area percentage of Compound E-5 was 99%. The product was further subjected to silica gel column chromatography, so that a purified product was obtained.

The $^1$H-NMR data of Compound E-5 obtained are as follows:

$^1$H-NMR (CDCl$_3$, TMS) δ (ppm): 2.29 (s, 3H), 7.70 (dd, 1H, J=8.0, 2.1 Hz), 7.78 (bs, 1H), 7.81 (d, 1H, J=2.7 Hz), 8.60 (d, 1H, J=8.0 Hz).

Example 7

Synthesis of
N-acetyl-2,3-dimethyl-4-trichloromethylthioaniline

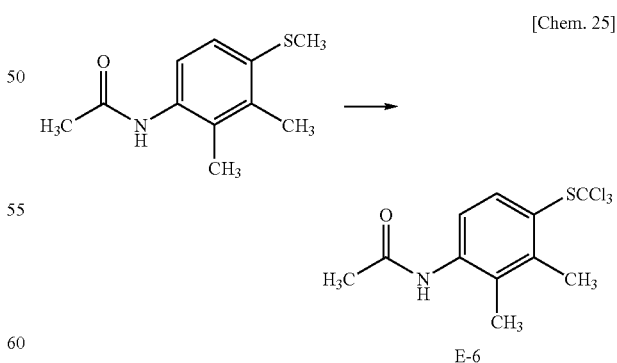

[Chem. 25]

To a mixture of 1.68 g of N-acetyl-2,3-dimethyl-4-methylthioaniline and 5.07 g of chlorobenzene was dropped a mixture of 3.57 g of sulfuryl chloride and 5.02 g of chlorobenzene at room temperature over 60 minutes. After the mixture was stirred at 20 to 30° C. for 3 hours, it was heated to 40° C.

and was stirred for 2.5 hours. The resulting mixture was further heated to 50° C. and stirred for 5.5 hours. After the mixture was cooled to room temperature, the reaction mixture was added to 10.52 g of water to be washed, followed by making phase-separation. The aqueous layer was extracted twice with 5.1 g of ethyl acetate. The organic layers were combined, and then washed successively with 10.0 g of saturated aqueous sodium bicarbonate solution and 7.5 g of saturated brine. The organic layer was dried over magnesium sulfate and then concentrated, so that 2.48 g of a product containing N-acetyl-2,3-dimethyl-4-trichloromethylthioaniline (Compound E-6) was obtained. The product was analyzed by HPLC to be found that the HPLC area percentage of Compound E-6 was 69%. The product was further subjected to silica gel column chromatography, so that a purified product was obtained.

The $^1$H-NMR data of Compound E-6 obtained are as follows:

$^1$H-NMR (CDCl$_3$, TMS) δ (ppm): 2.21 (s, 3H), 2.24 (s, 3H), 2.43 (s, 3H), 2.61 (s, 3H), 7.39 (d, 1H, J=8.8 Hz), 7.72 (d, 1H, J=8.8 Hz).

Example 8

Synthesis of
N-acetyl-2-fluoro-4-trifluoromethylthioaniline

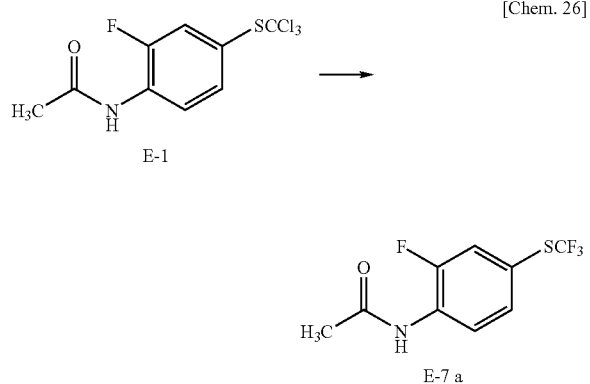

A reactor made of Teflon (registered trademark) was charged with a mixture of 0.38 g of N-acetyl-2-fluoro-4-trichloromethylthioaniline (Compound E-1) and 2.41 g of HF, and it was stirred at 0° C. for 2 hours and at room temperature for 20 hours. The resulting mixture was poured into 5.0 g of water that had been cooled to 0° C., and subsequently 5.0 g of ethyl acetate was added thereto. The mixture was neutralized by the addition of a saturated aqueous sodium bicarbonate solution, followed by making phase-separation. The ethyl acetate layer was washed twice with 5.0 g of water, so that an ethyl acetate solution containing N-acetyl-2-fluoro-4-trifluoromethylthioaniline (Compound E-7a) was obtained. The ethyl acetate solution containing Compound E-7a was analyzed by HPLC to be found that the HPLC area percentage of Compound E-7a was 42%.

The concentrate of the ethyl acetate solution is dissolved in a mixed liquid of concentrated hydrochloric acid and methanol (mass ratio 1:10), and the mixture is stirred at 65° C. for 6 hours. The reaction mixture is cooled to room temperature, poured into a saturated aqueous sodium bicarbonate solution, and extracted with ethyl acetate. The organic layer is dried over magnesium sulfate and then concentrated under reduced pressure, so that 2-fluoro-4-trifluoromethylthioaniline is obtained.

Example 9

Synthesis of
N-acetyl-2-fluoro-4-trifluoromethylthioaniline-2

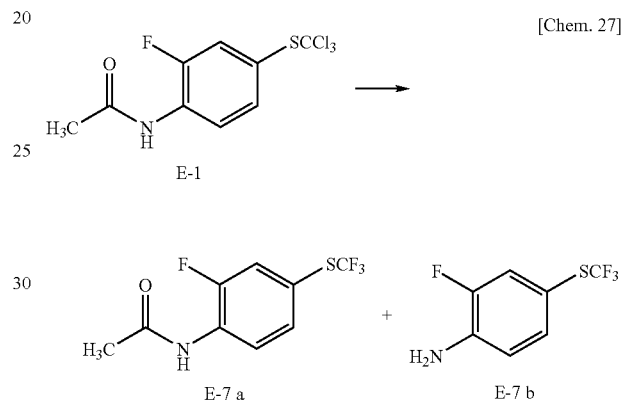

An autoclave was charged with a mixture of 0.38 g of N-acetyl-2-fluoro-4-trichloromethylthioaniline (Compound E-1) and 2.63 g of pyridine-18HF complex, and it was stirred at 90° C. for 2 hours and at 120° C. for 3 hours. The resulting mixture was cooled and poured into 5.0 g of water, and subsequently 5.0 g of ethyl acetate was added thereto. The mixture was neutralized by addition of a saturated aqueous sodium bicarbonate solution, followed by making phase-separation. The ethyl acetate layer was washed twice with 5.0 g of water, dried over magnesium sulfate, and then concentrated under reduced pressure, so that a product (0.24 g) containing N-acetyl-2-fluoro-4-trifluoromethylthioaniline (Compound E-7a) and 2-fluoro-4-trifluoromethylthioaniline (Compound E-7b; this is a deacetylated substance of Compound E-7a) was obtained. The product containing Compounds E-7a and E-7b was analyzed by HPLC to be found that the HPLC area percentage of Compound E-7a was 30.4% and the HPLC area percentage of Compound E-7b was 66.3%.

The concentrate of the ethyl acetate solution is dissolved in a mixed liquid of concentrated hydrochloric acid and methanol (mass ratio 1:10), and the mixture is stirred at 65° C. for 6 hours. The reaction mixture is cooled to room temperature, poured into a saturated aqueous sodium bicarbonate solution, and extracted with ethyl acetate. The organic layer is dried over magnesium sulfate and then concentrated under reduced pressure, so that 2-fluoro-4-trifluoromethylthioaniline (Compound E-7b) is obtained.

Example 10

Synthesis of N-acetyl-N-methyl-2-fluoro-4-trifluoromethylthioaniline

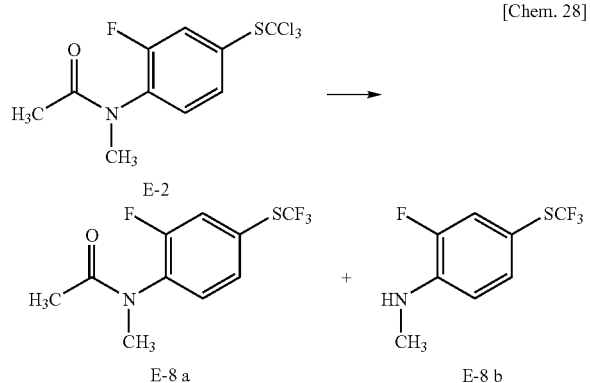

[Chem. 28]

An autoclave was charged with a mixture of 0.33 g of N-acetyl-N-methyl-2-fluoro-4-trichloromethylthioaniline (Compound E-2) and 2.19 g of pyridine-18HF complex, and it was stirred at 90° C. for 2 hour, at 120° C. for 2 hours, and subsequently at 150° C. for 2 hours. The resulting reaction mixture was cooled and poured into 5.0 g of water, and subsequently 5.0 g of ethyl acetate was added thereto. The mixture was neutralized by addition of a saturated aqueous sodium bicarbonate solution, followed making phase-separation. The ethyl acetate layer was washed twice with 5.0 g of water, so that an ethyl acetate solution containing N-acetyl-N-methyl-2-fluoro-4-trifluoromethylthioaniline (Compound E-8a) and N-methyl-2-fluoro-4-trifluoromethylthioaniline (Compound E-8b; this is a deacetylated substance of Compound E-8a) was obtained. The ethyl acetate solution containing Compounds E-8a and E-8b was analyzed by HPLC to be found that the HPLC area percentage of Compound E-8a was 25.8% and the HPLC area percentage of Compound E-8b was 64.6%.

The concentrate of the ethyl acetate solution is dissolved in a mixed liquid of concentrated hydrochloric acid and methanol (mass ratio 1:10), and the mixture is stirred at 65° C. for 6 hours. The reaction mixture is cooled to room temperature, poured into a saturated aqueous sodium bicarbonate solution, and extracted with ethyl acetate. The organic layer is dried over magnesium sulfate and then concentrated under reduced pressure, so that N-methyl-2-fluoro-4-trifluoromethylthioaniline (Compound E-8b) is obtained.

Example 11

Synthesis of N-trifluoroacetyl-2-fluoro-4-trifluoromethylthioaniline

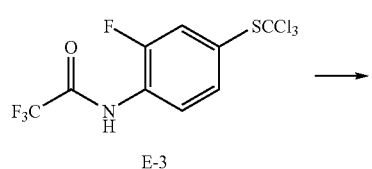

[Chem. 29]

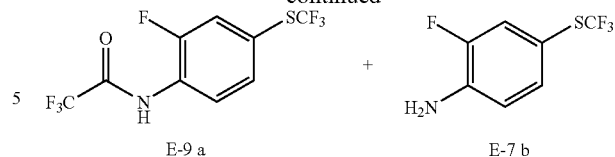

An autoclave was charged with a mixture of 0.29 g of N-trifluoroacetyl-2-fluoro-4-trichloromethylthioaniline (Compound E-3) and 2.07 g of pyridine-9HF, and it was stirred at 90° C. for 2 hour, at 120° C. for 2 hours, and at 150° C. for 2 hours. The resulting reaction mixture was analyzed by HPLC to be found that the HPLC area percentage of N-trifluoroacetyl-2-fluoro-4-trifluoromethylthioaniline (Compound E-9a) was 11.1% and the HPLC area percentage of 2-fluoro-4-trifluoromethylthioaniline (Compound E-7b; this is a detrifluoroacetylated substance of Compound E-9a) was 86.4%.

The aforementioned reaction mixture was poured into water, followed by extraction with ethyl acetate. The resulting organic layer was washed with water, and then dried over magnesium sulfate. The solvent was distilled off under reduced pressure. The resulting concentrate is dissolved in a mixed liquid of concentrated hydrochloric acid and methanol (mass ratio 1:10), and the mixture is stirred at 65° C. for 6 hours. The reaction mixture is cooled to room temperature, poured into a saturated aqueous sodium bicarbonate solution, and extracted with ethyl acetate. The organic layer is dried over magnesium sulfate and then concentrated under reduced pressure, so that 2-fluoro-4-trifluoromethylthioaniline (Compound E-7b) is obtained.

Example 12

Synthesis of N-formyl-2-fluoro-4-trifluoromethylthioaniline

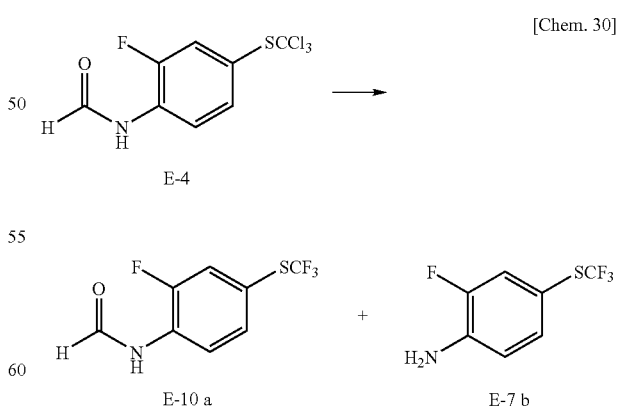

[Chem. 30]

An autoclave was charged with a mixture of 0.37 g of N-formyl-2-fluoro-4-trichloromethylthioaniline (Compound E-4) and 3.12 g of pyridine-9HF complex, and it was stirred at 90° C. for 2 hours, at 120° C. for 2 hours, and at 150° C. for 2 hours. The resulting reaction mixture was analyzed by HPLC to be found that the HPLC area percentage of 2-fluoro-4-trifluoromethylthioaniline (Compound E-7b; this is a deformylated substance of Compound E-10a) was 97.8%. N-formyl-2-fluoro-4-trifluoromethylthioaniline (Compound E-10a) was present in a very small amount.

After the reaction mixture obtained by the reaction is subjected to post-treatment, the resulting product is dissolved in a mixed liquid of concentrated hydrochloric acid and methanol (mass ratio 1:10), and the mixture is stirred at 65° C. for 6 hours. The reaction mixture is cooled to room temperature, poured into a saturated aqueous sodium bicarbonate solution, and extracted with ethyl acetate. The organic layer is dried over magnesium sulfate and then concentrated under reduced pressure, so that 2-fluoro-4-trifluoromethylthioaniline (Compound E-7b) is obtained.

Example 13

Synthesis of N-acetyl-2-chloro-4-trifluoromethylthioaniline

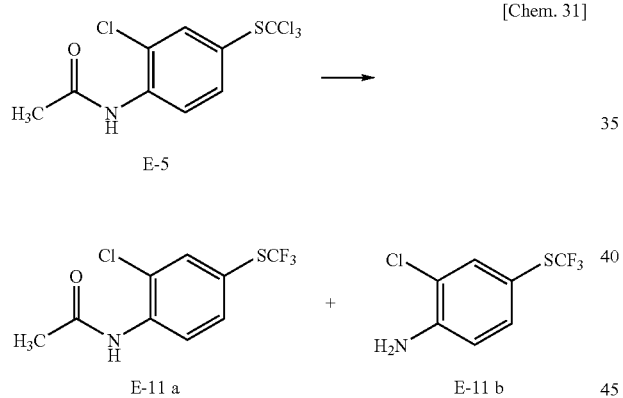

An autoclave was charged with a mixture of 0.35 g of N-acetyl-2-chloro-4-trichloromethylthioaniline (Compound E-5) and 2.60 g of pyridine-9HF complex, and it was stirred at 90° C. for 3 hours, at 120° C. for 3 hours, and at 150° C. for 2 hours. The resulting reaction mixture was analyzed by HPLC to be found that the HPLC area percentage of N-acetyl-2-chloro-4-trifluoromethylthioaniline (Compound E-11a) was 13.5% and that the HPLC area percentage of 2-chloro-4-trifluoromethylthioaniline (Compound E-11b; this is a deacetylated substance of Compound E-11a) was 84.4%.

The mass analysis data of Compounds E-11a and E-11b obtained are as follows:
E-11a: m/z=269 (M)$^+$
E-11b: m/z=227 (M)$^+$ The reaction mixture obtained by the aforementioned reaction was poured into water, followed by extraction with ethyl acetate. The organic layer was neutralized with a saturated aqueous sodium bicarbonate solution, washed with water, and then dried over magnesium sulfate. The solvent was distilled off under reduced pressure. The concentrate is dissolved in a mixed liquid of concentrated hydrochloric acid and methanol (mass ratio 1:10), and the resulting mixture is stirred at 65° C. for 6 hours. The reaction mixture is cooled to room temperature, poured into a saturated aqueous sodium bicarbonate solution, and extracted with ethyl acetate. The organic layer is dried over magnesium sulfate and then concentrated under reduced pressure, so that 2-chloro-4-trifluoromethylthioaniline (Compound E-11b) is obtained.

Example 14

Synthesis of N-acetyl-2,3-dimethyl-4-trifluoromethylthioaniline

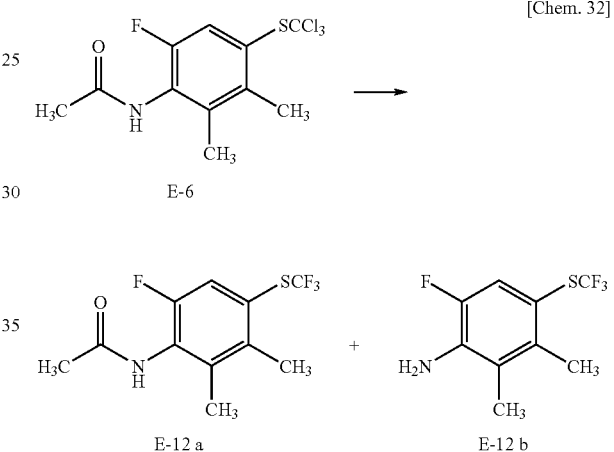

An autoclave was charged with a mixture of 0.30 g of N-acetyl-2,3-dimethyl-4-trichloromethylthioaniline (Compound E-6) and 2.23 g of pyridine-9HF complex, and it was stirred at 90° C. for 3 hours. The resulting reaction mixture was analyzed by HPLC to be found that the HPLC area percentage of N-acetyl-2,3-dimethyl-4-trifluoromethylthioaniline (Compound E-12a) was 33.1% and that the HPLC area percentage of 2,3-dimethyl-4-trifluoromethylthioaniline (Compound E-12b; this is a deacetylated substance of Compound E-12a) was 49.3%. The reaction mixture obtained by the aforementioned reaction was poured into water, followed by extraction with ethyl acetate. The organic layer was neutralized with a saturated aqueous sodium bicarbonate solution, washed with water, and then dried over magnesium sulfate. The solvent was distilled off under reduced pressure. The concentrate was dissolved in a mixed liquid of concentrated hydrochloric acid and methanol (mass ratio 1:10), and the mixture was stirred at 65° C. for 6 hours. The reaction mixture was cooled to room temperature, poured into a saturated aqueous sodium bicarbonate solution, and extracted with ethyl acetate. The organic layer was dried over magnesium sulfate and then concentrated under reduced pressure, so that 2,3-dimethyl-4-trifluoromethylthioaniline (Compound E-12b) was obtained.

The $^1$H-NMR data of Compound E-12b obtained are as follows:

$^1$H-NMR (CDCl$_3$, TMS) δ (ppm): 2.11 (s, 3H), 2.50 (s, 3H), 3.84 (bs, 2H), 6.55 (d, 1H, J=8.0 Hz), 7.36 (d, 1H, J=8.0 Hz).

Example 15

Synthesis of N-acetyl-N-methyl-2-fluoro-4-trifluoromethylthioaniline-2

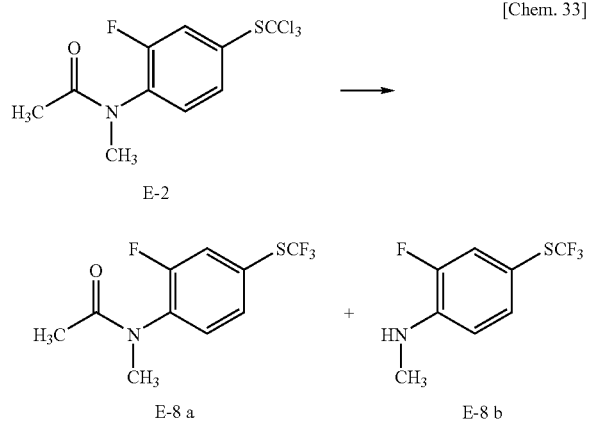

An autoclave was charged with a mixture of 0.32 g of N-acetyl-N-methyl-2-fluoro-4-trichloromethylthioaniline (Compound E-2) and 2.58 g of pyridine-9HF complex, and it was stirred at 90° C. for 1 hour, at 120° C. for 2 hours, and at 150° C. for 2 hours. The resulting reaction mixture was cooled and poured into 3.2 g of water, and subsequently 4.0 g of ethyl acetate was added thereto. The mixture was neutralized by addition of a saturated aqueous sodium bicarbonate solution, followed by making phase-separation. The ethyl acetate layer was washed twice with 5.0 g of water, dried over magnesium sulfate, and then concentrated under reduced pressure, so that 0.20 g of a product containing N-acetyl-N-methyl-2-fluoro-4-trifluoromethylthioaniline (Compound E-8a) and N-methyl-2-fluoro-4-trifluoromethylthioaniline (Compound E-8b; this is a deacetylated substance of Compound E-8a) was obtained. The HPLC area percentage of Compound E-8a was 21.0% and the HPLC area percentage of Compound E-8b was 72.2%. Subsequently, 0.19 g of the aforementioned resulting product was dissolved in a mixed liquid of 0.2 g of concentrated hydrochloric acid and 2.0 g of methanol, and the mixture was stirred at 65° C. for 6 hours. The reaction mixture was cooled to room temperature, and 25 g of a saturated aqueous sodium bicarbonate solution and 30 g of ethyl acetate were added thereto, and then extracted. The organic layer was dried over magnesium sulfate and concentrated under reduced pressure, so that 0.13 g of N-methyl-2-fluoro-4-trifluoromethylthioaniline (Compound E-8b) was obtained. The GC area percentage was 95.5%.

The $^1$H-NMR data of Compound E-8b obtained are as follows:

$^1$H-NMR (CDCl$_3$, TMS) δ (ppm): 2.91 (m, 3H), 4.27 (br, 1H), 6.62-6.67 (m, 1H), 7.23-7.33 (m, 2H).

Example 16

Synthesis-2 of N-acetyl-2-fluoro-4-trifluoromethylthioaniline

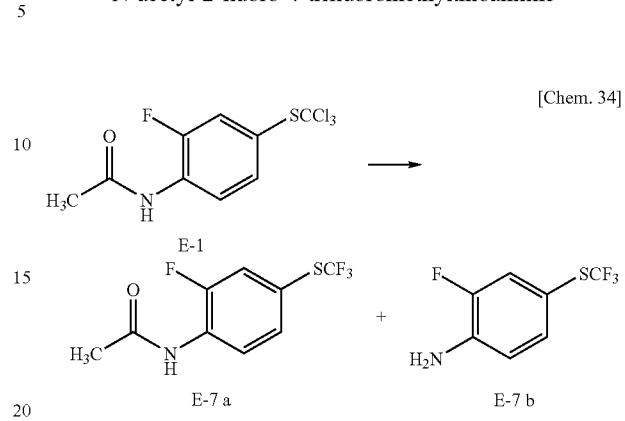

An autoclave was charged with a mixture of 0.48 g of N-acetyl-2-fluoro-4-trichloromethylthioaniline (Compound E-1) and 2.10 g of triethylamine-3HF complex, and it was stirred at 60° C. for 1 hour, subsequently at 120° C. for 2 hours, and subsequently at 180° C. for 3 hours. The resulting reaction mixture was cooled and poured into 2.27 g of water, and subsequently was extracted with 4.60 g of ethyl acetate. The ethyl acetate layer was washed with water and an aqueous sodium bicarbonate solution, dried over magnesium sulfate, and then concentrated under reduced pressure, so that a product (0.37 g) containing N-acetyl-2-fluoro-4-trifluoromethylthioaniline (Compound E-7a) and 2-fluoro-4-trifluoromethylthioaniline (Compound E-7b; this is a deacetylated substance of Compound E-7a) was obtained. The HPLC area percentage of Compound E-7a was 51% and the HPLC area percentage of Compound E-7b was 29%.

The $^1$H-NMR data of Compounds E-7a and E-7b are as follows:

Compound E-7a;

$^1$H-NMR (CDCl$_3$, TMS) δ (ppm): 2.25 (s, 3H), 7.3-7.4 (m, 3H), 8.46 (t, 1H).

Compound E-7b;

$^1$H-NMR (CDCl$_3$, TMS) δ (ppm): 3.8-4.2 (br, 2H), 6.75 (t, 1H), 7.2-7.3 (m, 2H).

Comparative Example 1

Synthesis of 2-fluoro-4-trichloromethylthioaniline

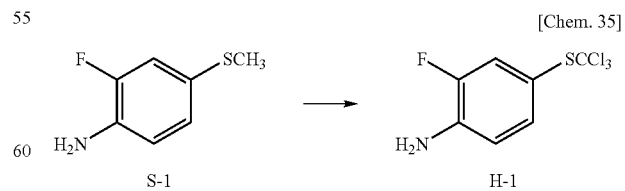

To a mixture of 1.21 g of 2-fluoro-4-methylthioaniline (Compound S-1) and 3.49 g of chlorobenzene was dropped a mixture of 3.37 g of sulfuryl chloride and 3.50 g of chlorobenzene at room temperature over 30 minutes. After the reaction mixture was stirred at 20 to 25° C. for 1.5 hours, it was heated to 60 to 65° C. and was stirred for 4 hours. The resulting reaction mixture was analyzed by GC to be found that the GC area percentage of 2-fluoro-4-trichloromethylmethylthioaniline (Compound H-1) was 2.1% and that the GC area percentage of Compound S-1, which was a raw material, was 3.7%.

Comparative Example 2

Synthesis of N-benzoyl-2-fluoro-4-trichloromethylthioaniline

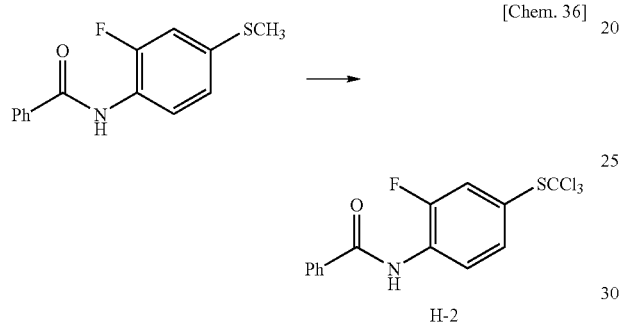

H-2

To a mixture of 3.16 g of N-benzoyl-2-fluoro-4-methylthioaniline and 9.40 g of chlorobenzene was dropped a mixture of 5.40 g of sulfuryl chloride and 9.39 g of chlorobenzene at room temperature over 40 minutes. The reaction mixture was heated to 60 to 65° C. and was stirred for 4 hours. When the resulting reaction mixture was analyzed by GC, peaks of many products were detected and it was difficult to identify the peak of N-benzoyl-2-fluoro-4-trichloromethylthioaniline (Compound H-2).

The analysis conditions of GC and HPLC are as follows.

(1) Gas Chromatography (GC)

GC instrument: Shimadzu GC-14A; integrator: Shimadzu CR8A; column: DB-5 (1.5 μm in film thickness, 30 m in length, and 0.53 mm in internal diameter); column temperature conditions: the column is heated from 50° C. to 70° C. at a rate of 5° C./min, subsequently heated to 250° C. at a rate of 10° C./min, subsequently heated to 280° C. at a rate of 15° C./min, and held at 280° C. for 10 minutes; injection temperature: 280° C.; detector temperature: 250° C.; carrier gas: helium 5 ml/min.

(2) High-Performance Liquid Chromatography (HPLC)

LC instrument: Hitachi LC-7100; integrator: Hitachi LC-7500; column: ODS L-Column 4.6 mmφ×150 mm; mobile phase: A liquid (0.1% phosphoric acid water), B liquid (acetonitrile); gradient condition: the A liquid/B liquid ratio was changed from 90/10 to 9/91 in 27 min, and was hold at 9/91 for 10 min; flow rate: 1.0 mL/min; column temperature: 40° C.; detection wavelength: 254 nm; injection amount: 10 μL.

The invention claimed is:

1. A method for producing a 4-(trichloromethylthio)aniline, comprising a step of making a 4-(methylthio)aniline represented by the general formula (I):

[Chem. 1]

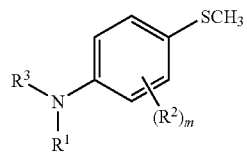

(I)

wherein $R^1$ represents a hydrogen atom or an alkyl group having 1 to 3 carbon atoms, $R^2$ each independently represents a halogen atom, an alkyl group having 1 to 3 carbon atoms, or a perfluoroalkyl group having 1 to 3 carbon atoms, $R^3$ represents a formyl group, an acetyl group, or a trifluoroacetyl group, and m represents an integer of 0 to 4, react with sulfuryl chloride to obtain a 4-(trichloromethylthio)aniline represented by the general formula (II):

[Chem. 2]

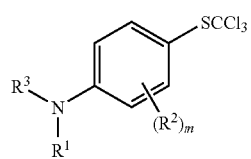

(II)

wherein $R^1$, $R^2$, $R^3$, and m are the same in meaning as those defined above.

2. The method according to claim 1, wherein $R^3$ in the general formula (I) is an acetyl group.

3. A method for producing a 4-(trifluoromethylthio)aniline, comprising steps of:

making a 4-(methylthio)aniline represented by the general formula (I):

[Chem. 3]

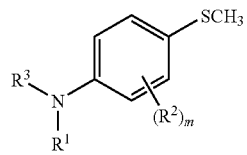

(I)

wherein $R^1$ represents a hydrogen atom or an alkyl group having 1 to 3 carbon atoms, $R^2$ each independently represents a halogen atom, an alkyl group having 1 to 3 carbon atoms, or a perfluoroalkyl group having 1 to 3 carbon atoms, $R^3$ represents a formyl group, an acetyl group, or a trifluoroacetyl group, and m represents an integer of 0 to 4, react with sulfuryl chloride to obtain a 4-(trichloromethylthio)aniline represented by the general formula (II):

[Chem. 4]

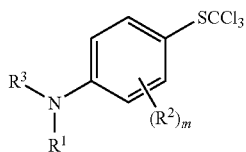

(II)

wherein $R^1$, $R^2$, $R^3$, and m are the same in meaning as those defined above, and making the 4-(trichloromethylthio)aniline represented by the general formula (II) react with a fluorinating agent to obtain a 4-(trifluoromethylthio)aniline represented by the general formula (III):

[Chem. 5]

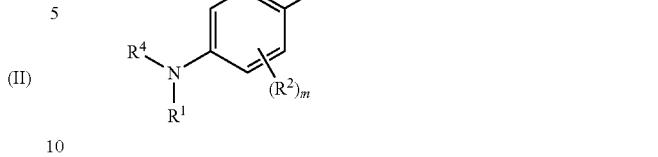

(III)

wherein $R^1$, $R^2$, and m are the same in meaning as those defined above, and $R^4$ represents a hydrogen atom, a formyl group, an acetyl group, or a trifluoroacetyl group.

4. The method according to claim 3, wherein the fluorinating agent is hydrogen fluoride and/or a hydrogen fluoride-amine complex.

5. The method according to claim 3, wherein $R^3$ in the general formula (II) is an acetyl group.

6. The method according to claim 4, wherein $R^3$ in the general formula (II) is an acetyl group.

* * * * *